(12) United States Patent
Tsutsui et al.

(10) Patent No.: US 10,531,026 B2
(45) Date of Patent: Jan. 7, 2020

(54) ENDOSCOPE SYSTEM (71) Applicant: OLYMPUS CORPORATION, Tokyo (JP)

(72) Inventors: Keisuke Tsutsui, Kawaguchi (JP); Fumiyuki Okawa, Tama (JP)

(73) Assignee: OLYMPUS CORPORATION, Tokyo (JP)

( * ) Notice: Subject to any disclaimer, the term of this patent is extended or adjusted under 35 U.S.C. 154(b) by 141 days.

(21) Appl. No.: 15/474,143

(22) Filed: Mar. 30, 2017

(65) Prior Publication Data

US 2017/0208267 A1    Jul. 20, 2017

Related U.S. Application Data (63) Continuation of application No. PCT/JP2016/054733, filed on Feb. 18, 2016.

(30) Foreign Application Priority Data

May 29, 2015   (JP) ................................. 2015-110321

(51) Int. Cl.
*H04N 5/357*   (2011.01)
*A61B 1/00*   (2006.01)
(Continued)

(52) U.S. Cl.
CPC ......... *H04N 5/357* (2013.01); *A61B 1/00006* (2013.01); *A61B 1/045* (2013.01);
(Continued)

(58) Field of Classification Search
None
See application file for complete search history.

(56) References Cited

U.S. PATENT DOCUMENTS

2011/0242300 A1   10/2011   Hashimoto

FOREIGN PATENT DOCUMENTS

JP   2011-206335 A   10/2011
JP   2011-206337 A   10/2011
(Continued)

OTHER PUBLICATIONS

International Search Report dated May 24, 2016 issued in PCT/JP2016/054733.

*Primary Examiner* — James M Anderson, II
(74) *Attorney, Agent, or Firm* — Scully, Scott, Murphy & Presser, P.C.

(57) ABSTRACT

An endoscope system includes: an image pickup device for picking up an object image; a drive control circuit for initializing and driving the image pickup device; and a monitoring portion for detecting abnormality of an image pickup signal from the image pickup device and outputting an initialization start signal to the drive control circuit. The monitoring portion compares a synchronization code, an optical black pixel value and an effective pixel value of the image pickup signal with respective thresholds indicating a normal range and a stipulated number of times or a stipulated number of pieces, and in a case of detecting abnormality of one of the synchronization code, the optical black pixel value and the effective pixel value, outputs the initialization start signal to the drive control circuit, and the drive control circuit initializes the image pickup device in a case of receiving the initialization start signal the monitoring portion.

8 Claims, 8 Drawing Sheets (51) Int. Cl.
    *A61B 1/045*     (2006.01)
    *A61B 1/05*     (2006.01)
    *G02B 23/24*     (2006.01)
    *H04N 5/225*     (2006.01)
    *H04N 5/374*     (2011.01)

(52) U.S. Cl.
    CPC .......... *A61B 1/051* (2013.01); *G02B 23/2484* (2013.01); *H04N 5/2252* (2013.01); *H04N 5/374* (2013.01)

(56) References Cited

FOREIGN PATENT DOCUMENTS

| | | | |
|---|---|---|---|
| JP | 2011-250938 A | | 12/2011 |
| JP | 2011250938 A | * | 12/2011 |
| JP | 2013-172904 A | | 9/2013 |
| JP | 2013172904 A | * | 9/2013 |

* cited by examiner

ENDOSCOPE SYSTEM

CROSS REFERENCE TO RELATED APPLICATION

This application is a continuation application of PCT/JP2016/054733 filed on Feb. 18, 2016 and claims benefit of Japanese Application No. 2015-110321 filed in Japan on May 29, 2015, the entire contents of which are incorporated herein by this reference.

BACKGROUND OF THE INVENTION

1. Field of the Invention

The present invention relates to an endoscope system, and relates in particular to an endoscope system that detects abnormality of an image pickup signal and initializes an image pickup device.

2. Description of the Related Art

Conventionally, an endoscope system including an endoscope, which inserts an elongated endoscope into a body cavity or the like and performs observation of a part to be examined and various kinds of treatment has been widely used. As such an endoscope system, for example, Japanese Patent Application Laid-Open Publication No. 2011-206337 discloses an endoscope system including an electronic endoscope provided with a solid-state image pickup device, and a processor device connected to the electronic endoscope and configured to execute various kinds of signal processing to an image pickup signal from the solid-state image pickup device and perform conversion to image data. Then, the image data converted by the processor device is displayed on a monitor connected to the processor device via a cable.

As the solid-state image pickup device loaded on such an electronic endoscope, a CCD type solid-state image pickup device has been generally used conventionally, however, a CMOS type solid-state image pickup device has been also used in recent years. The CMOS type solid-state image pickup device includes a register for storing setting values (control data) of drive and read operations or the like, and the drive and read operations are performed based on the control data set in the register. The control data is transmitted from the processor device to the electronic endoscope, and set in the register of the CMOS type solid-state image pickup device.

Now, for the endoscope system, sometimes a surgical instrument such as an electrocautery is also used during endoscopic observation, and the control data is sometimes rewritten to an unintended value due to disturbance noise from the electrocautery or the like while the control data is transmitted or after the control data is stored in the register. In this way, in a case that the control data is rewritten due to the disturbance noise or the like, abnormality sometimes occurs in the drive and read operations of the CMOS type solid-state image pickup device.

Therefore, in the endoscope system in Japanese Patent Application Laid-Open Publication No. 2011-206337, the control data stored in the register is superimposed on the image pickup signal outputted from the CMOS type solid-state image pickup device and transmitted to the processor device. Then, the endoscope system, in the processor device, compares the control data superimposed on the image pickup signal with the control data set in the register, and detects whether or not the control data stored in the register is rewritten.

In the case of detecting that the setting value is rewritten, the endoscope system retransmits the control data from the processor device to the CMOS type solid-state image pickup device of the electronic endoscope. That is, in the case of detecting abnormality of the control data stored in the register, normal control data is transmitted to the register of the CMOS type solid-state image pickup device, the control data of the register is reset, and the drive and read operations of the CMOS type solid-state image pickup device are returned to be normal.

In this way, in the case that the control data set in the register of the CMOS type solid-state image pickup device is rewritten to an abnormal value due to influence of the disturbance noise or the like, by setting the normal control data in the register again, the drive and read operations of the CMOS type solid-state image pickup device can be returned to be normal.

In addition, Japanese Patent Application Laid-Open Publication No. 2013-172904 discloses an image pickup apparatus that superimposes a discrimination signal generated by each portion of an image pickup device on an optical black region or a blanking period (blanking region between synchronizing signals) and discriminates an abnormal part based on the signal to which the determination signal of the each portion is added. Thus, in the image pickup apparatus, the abnormal part of the image pickup device is specified in detail.

SUMMARY OF THE INVENTION

An endoscope system of one aspect of the present invention includes: an image pickup device configured to pick up an image of an object; a drive control portion configured to initialize and drive the image pickup device; and a monitoring portion configured to detect abnormality of an image pickup signal from the image pickup device and output an initialization start signal to the drive control portion. The monitoring portion compares a synchronization code, an optical black pixel value and an effective pixel value of the image pickup signal from the image pickup device with respective thresholds indicating a normal range and a stipulated number of times or a stipulated number of pieces, and in a case of detecting abnormality of one of the synchronization code, the optical black pixel value and the effective pixel value, outputs the initialization start signal to the drive control portion, and the drive control portion initializes the image pickup device in a case that the initialization start signal is inputted from the monitoring portion.

DETAILED DESCRIPTION OF THE PREFERRED EMBODIMENT(S)

Hereinafter, embodiments of the present invention will be described in detail with reference to the drawings.

First Embodiment

Figure 1:
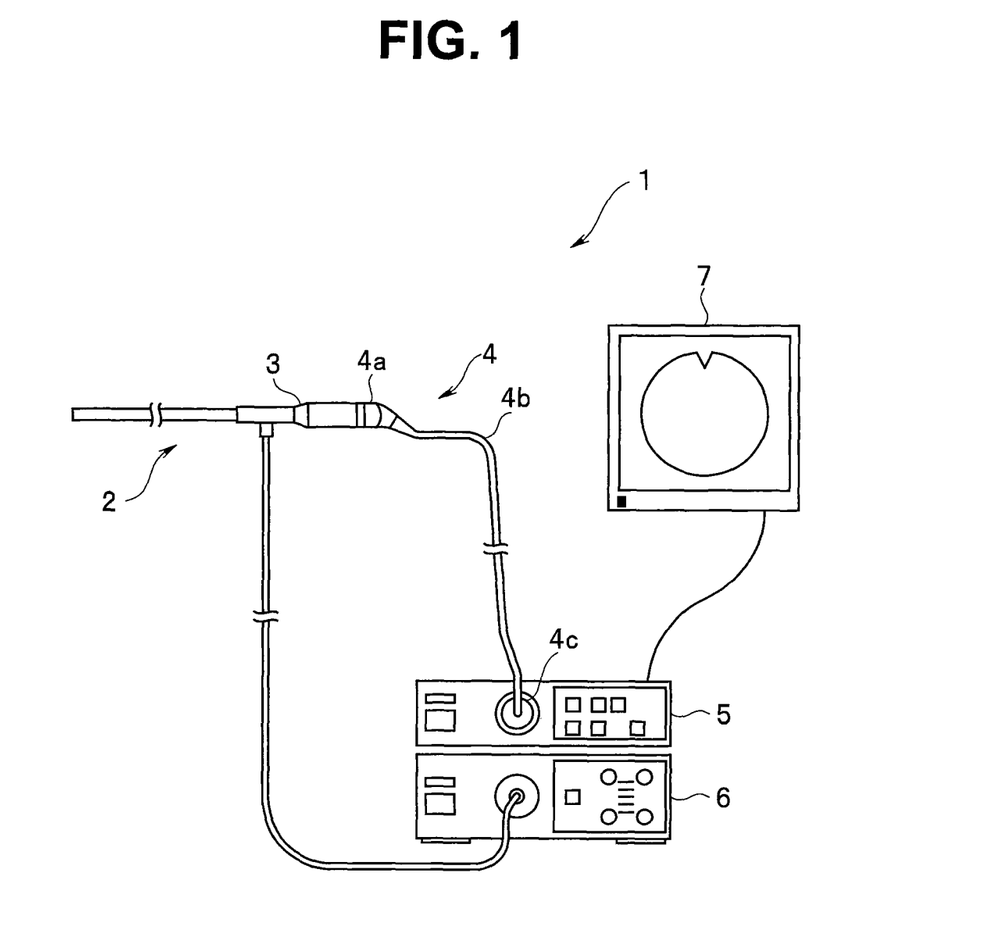
FIG. 1 is a diagram illustrating a configuration of an endoscope system relating to a first embodiment.
Figure 2:
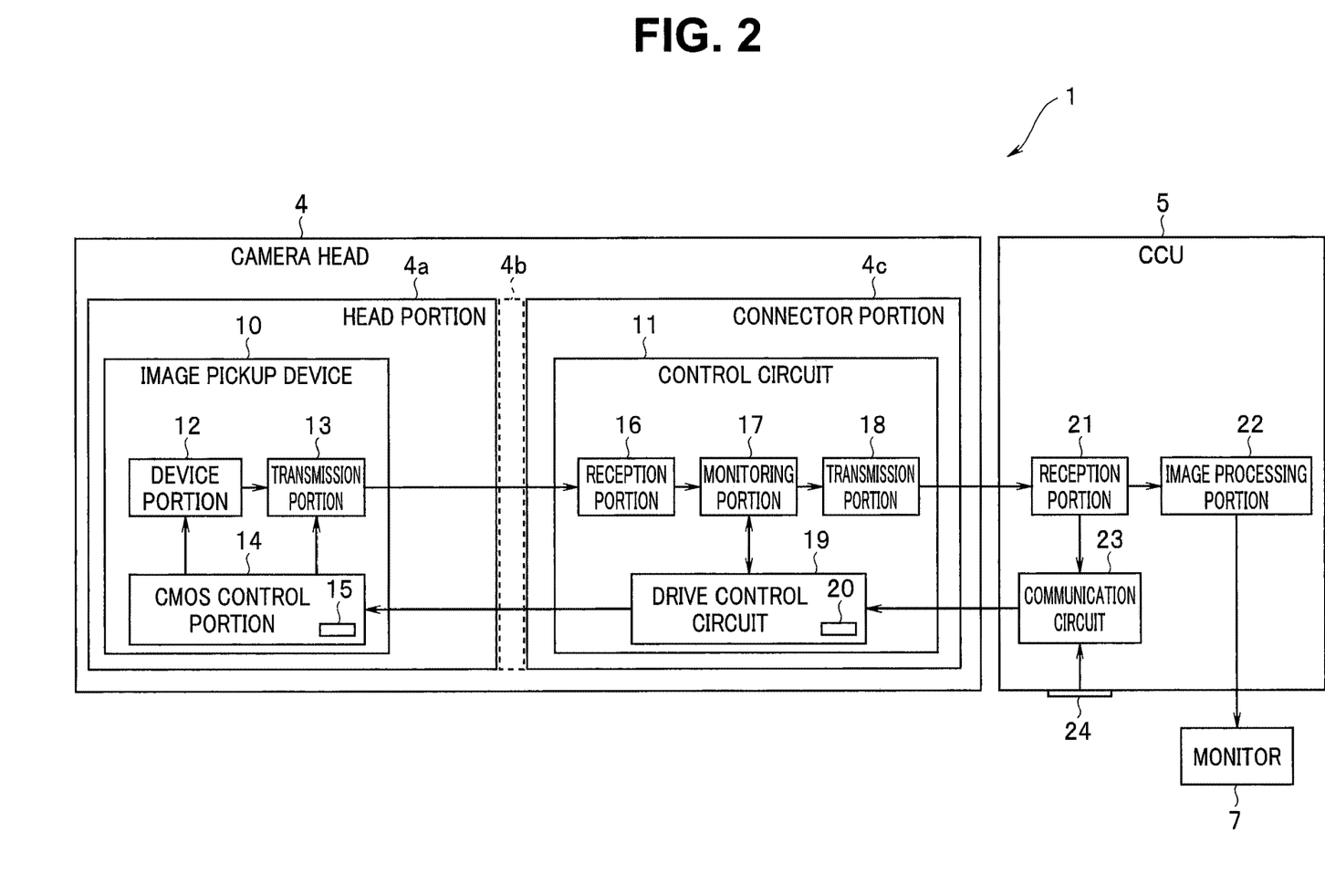
FIG. 2 is a diagram illustrating a detailed circuit configuration of a camera head and a camera control unit of the endoscope system relating to the first embodiment.
Figure 3:
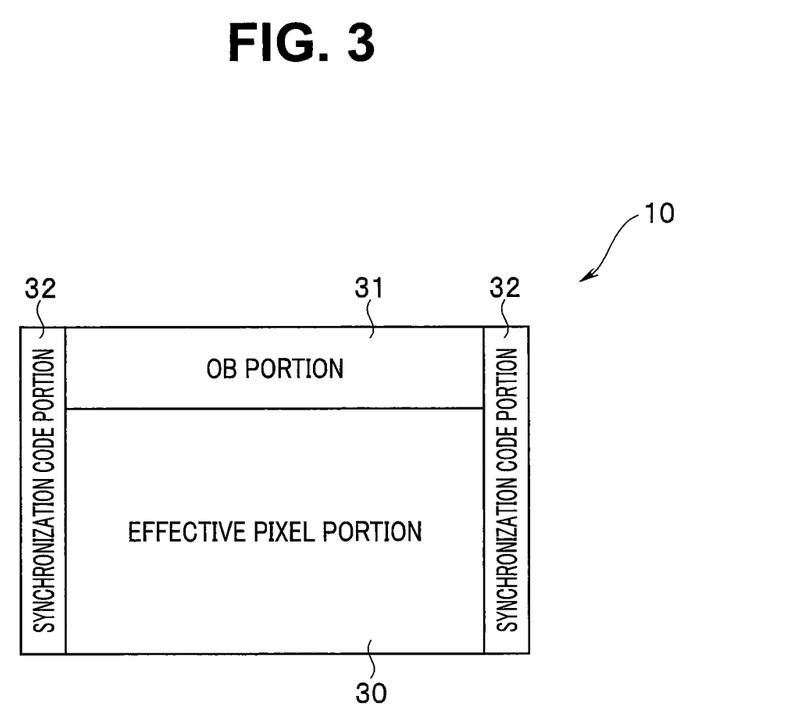
FIG. 3 is a diagram for describing an example of an output format of an image pickup device.
Figure 4:
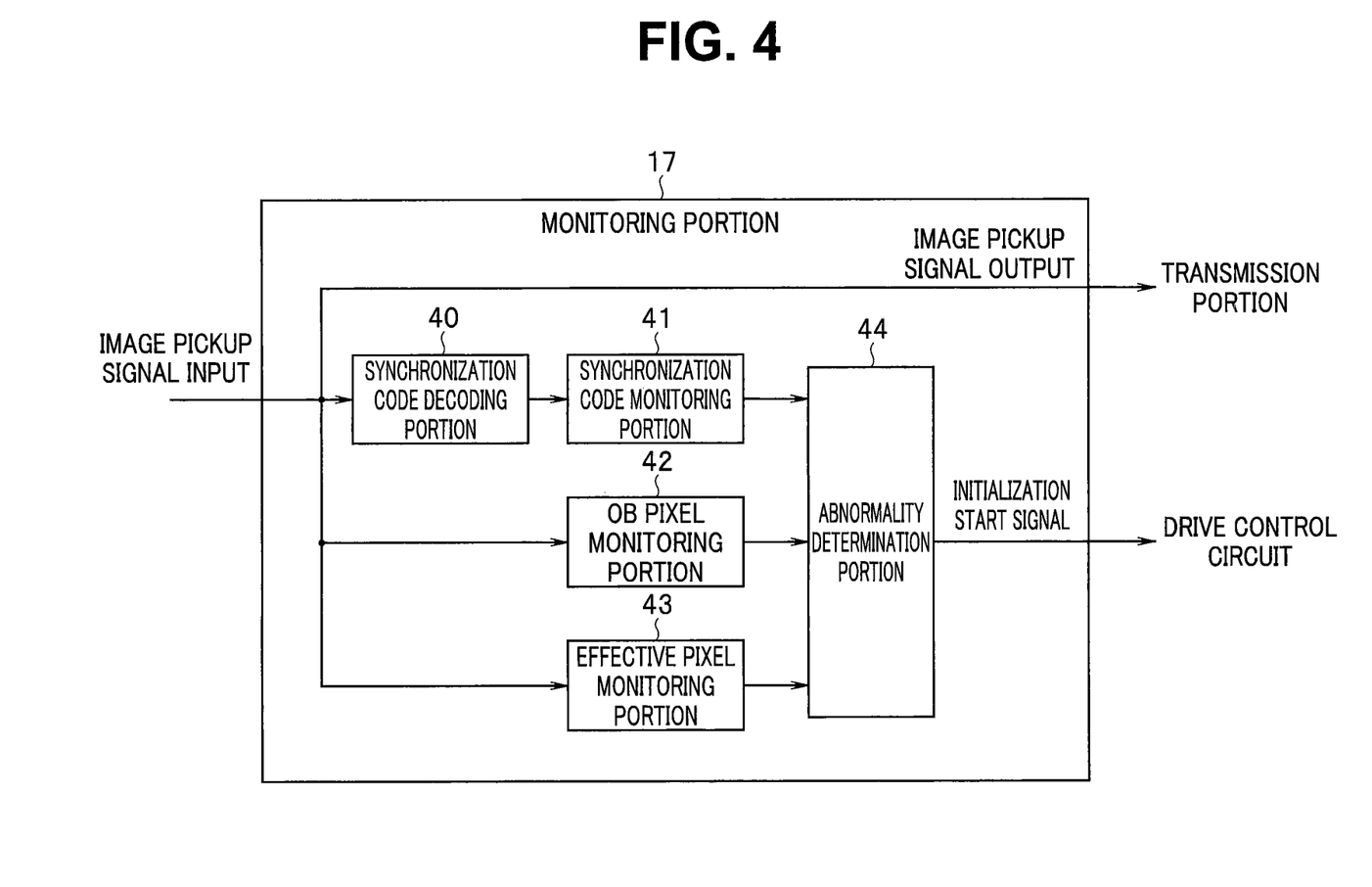
FIG. 4 is a diagram illustrating a detailed circuit configuration of a monitoring portion.

FIG. 1 is a diagram illustrating a configuration of an endoscope system relating to a first embodiment, FIG. 2 is a diagram illustrating a detailed circuit configuration of a camera head and a camera control unit of the endoscope system relating to the first embodiment, FIG. 3 is a diagram for describing an example of an output format of an image pickup device, and FIG. 4 is a diagram illustrating a detailed circuit configuration of a monitoring portion.

As illustrated in FIG. 1, an endoscope system 1 is configured including an endoscope 2 of an optical type for example, a camera head 4 freely attachably and detachably connected to an eyepiece portion 3 of the endoscope 2, a camera control unit (referred to as a CCU, hereinafter) 5 to which the camera head 4 is freely attachably and detachably connected, a light source device 6 configured to supply illumination light to the endoscope 2, and a monitor 7 configured to receive input of a video signal generated in an image processing portion to be described later of the CCU 5 and display an observation image.

The camera head 4 includes a head portion 4a connected to the eyepiece portion 3, a cable 4b extended from the head portion 4a, and a connector portion 4c provided on a proximal end portion of the cable 4b. The camera head 4 is connected to the CCU 5 through the connector portion 4c.

Note that, while description is given assuming that the camera head 4 is connected to the endoscope 2, other camera heads of different specifications such as a magnification ratio may be also connected. In addition, to the CCU 5, an electronic endoscope may be also connected.

As illustrated in FIG. 2, the head portion 4a is configured including an image pickup device 10 configured by a CMOS type solid-state image pickup device and configured to pick up an image of an object. In addition, the connector portion 4c is configured including a control circuit 11 configured to monitor a read signal from the image pickup device 10 and initialize the image pickup device 10 again when abnormality is present in the read signal from the image pickup device 10.

The image pickup device 10 is configured including a device portion 12, a transmission portion 13, and a CMOS control portion 14 configured to control the device portion 12 and the transmission portion 13. The CMOS control portion 14 includes a register 15 configured to hold setting values for controlling the device portion 12 and the transmission portion 13.

Furthermore, the control circuit 11 is configured including a reception portion 16, a monitoring portion 17, a transmission portion 18, and a drive control circuit 19. The drive control circuit 19 includes a nonvolatile memory 20 configured to hold a list of the setting values (thresholds to be described later) to be set to the monitoring portion 17.

In addition, the CCU 5 is configured including a reception portion 21, an image processing portion 22, a communication circuit 23, and an operation portion 24. The CCU 5 can rewrite (change) the setting value set in the memory 20 through the operation portion 24.

When a user operates the operation portion 24 and instructs rewrite of the setting value, the communication circuit 23 communicates with the drive control circuit 19. Then, the communication circuit 23 transmits a newly set setting value to the drive control circuit 19 to rewrite the setting value in the memory 20. Note that the setting value may be rewritten using a personal computer or the like, not shown, connected to the CCU 5.

The illumination light from the light source device 6 is transmitted to the endoscope 2 through a light guide not shown, and radiated from a distal end face of an insertion portion to the object through the light guide, not shown, inside the insertion portion. An image of return light from the object is picked up by the device portion 12 of the image pickup device 10 of the head portion 4a. An image pickup signal picked up by the device portion 12 of the image pickup device 10 is outputted to the transmission portion 13.

The CMOS control portion 14 superimposes a synchronization code on the image pickup signal from the device portion 12, in the transmission portion 13. The transmission portion 13 converts the image pickup signal on which the synchronization code is superimposed from parallel to serial, and transmits the signal to the reception portion 16 of the control circuit 11 as LVDS (low voltage differential signal).

The reception portion 16 converts the received image pickup signal from serial to parallel, and outputs the signal to the monitoring portion 17. The monitoring portion 17 outputs the image pickup signal from the reception portion 16 to the transmission portion 18, and monitors whether or not abnormality is present in the image pickup signal. In addition, in the case of detecting that the abnormality is present in the image pickup signal, the monitoring portion 17 outputs the initialization start signal to the drive control circuit 19. When the initialization start signal is inputted from the monitoring portion 17, the drive control circuit 19 as a drive control portion initializes the image pickup device 10 again. Note that abnormality detection of the image pickup signal will be described later.

The transmission portion 18 converts the inputted image pickup signal from parallel to serial, and transmits the signal to the reception portion 21 of the CCU 5 as the LVDS. The reception portion 21 converts the received image pickup signal from serial to parallel, and outputs the signal to the image processing portion 22.

The image processing portion 22 generates video signal by executing predetermined image processing to the inputted image pickup signal and outputs the generated video signal to the monitor 7 and thus, the observation image is displayed on the monitor 7.

The image pickup device 10 is, as illustrated in FIG. 3, configured by an effective pixel portion 30 as an effective pixel region where an object image is photoelectrically converted, an OB portion 31 as an optical black (referred to as OB, hereinafter) region for detecting a black level, and synchronization code portions 32. Note that the OB portion 31 is arranged at an upper part of the effective pixel portion 30, however, without being limited to the upper part, may be arranged in either one of right and left regions of the effective pixel portion 30 or in both of the right and left regions of the effective pixel portion 30, for example.

Before and after pixels for one line read from the effective pixel portion 30 and the OB portion 31, the synchronization code portions 32 where the synchronization code for detecting start of horizontal synchronization and start of horizontal blanking respectively is superimposed is arranged. The synchronization code is superimposed in the transmission portion 13 by control of the CMOS control portion 14.

As illustrated in FIG. 4, the monitoring portion 17 is configured including a synchronization code decoding portion 40, a synchronization code monitoring portion 41, an OB pixel monitoring portion 42, an effective pixel monitoring portion 43, and an abnormality determination portion 44.

The image pickup signal inputted to the monitoring portion 17 is outputted to the transmission portion 18 as image pickup signal output. In addition, the image pickup signal inputted to the monitoring portion 17 is inputted to the synchronization code decoding portion 40, the OB pixel monitoring portion 42, and the effective pixel monitoring portion 43.

The synchronization code decoding portion 40 decodes the synchronization code of the synchronization code portion 32 of the inputted image pickup signal and outputs the synchronization code to the synchronization code monitoring portion 41. The synchronization code monitoring portion 41 periodically monitors a number of times of receiving the synchronization code within a constant time period, and outputs a monitoring result to the abnormality determination portion 44. More specifically, the synchronization code monitoring portion 41 outputs an abnormality signal to the abnormality determination portion 44 in the case that the number of times of detecting the synchronization code within the constant time period is off a threshold indicating a predetermined number of times of reception and the number of times of detecting the synchronization code off the threshold exceeds a certain threshold width indicating a normal range. The constant time period may be configured to be varied in linkage with a read cycle (frame rate) of the image pickup signal.

The OB pixel monitoring portion 42 monitors whether or not a value other than assumed signals is present in OB pixel values of the OB portion 31, and outputs a monitoring result to the abnormality determination portion 44. More specifically, the OB pixel monitoring portion 42 outputs the abnormality signal to the abnormality determination portion 44 in the case that the OB pixel value is off a predetermined threshold indicating the normal range and the number of OB pixels off the predetermined threshold exceeds a stipulated number of pieces. The monitoring portion determines abnormality within a frame in which the image pickup signal is read.

The effective pixel monitoring portion 43 monitors whether or not the value other than assumed signals is present in effective pixel values of the effective pixel portion 30, and outputs a monitoring result to the abnormality determination portion 44. More specifically, the effective pixel monitoring portion 43 outputs the abnormality signal to the abnormality determination portion 44 in the case that the effective pixel value is off the predetermined threshold indicating the normal range and the number of the effective pixels off the predetermined threshold exceeds the stipulated number of pieces. The monitoring portion determines abnormality within a frame in which the image pickup signal is read.

In the case that one of the synchronization code monitoring portion 41, the OB pixel monitoring portion 42 and the effective pixel monitoring portion 43 outputs the abnormality signal, the abnormality determination portion 44 outputs the initialization start signal to the drive control circuit 19.

When the initialization start signal is inputted from the monitoring portion 17, the drive control circuit 19 executes initialization processing of the image pickup device 10. In addition, the drive control circuit 19 outputs detection a possibility signal to the monitoring portion 17 so as not to detect the abnormality in a period during which the initialization start signal is inputted and the initialization of the image pickup device 10 is executed. In the period of executing the initialization, it is possible that a signal different from normal image pickup signal is outputted from the image pickup device 10. Therefore, when the abnormality is determined even in the period of executing the initialization, there is a risk that the initialization start signal is outputted at all times from the abnormality determination portion 44 to the drive control circuit 19 and the drive control circuit 19 continuously executes the initialization of the image pickup device 10.

Here, abnormality determination processing of the image pickup device 10 of the endoscope system 1 configured in this way will be described.

Figure 5:
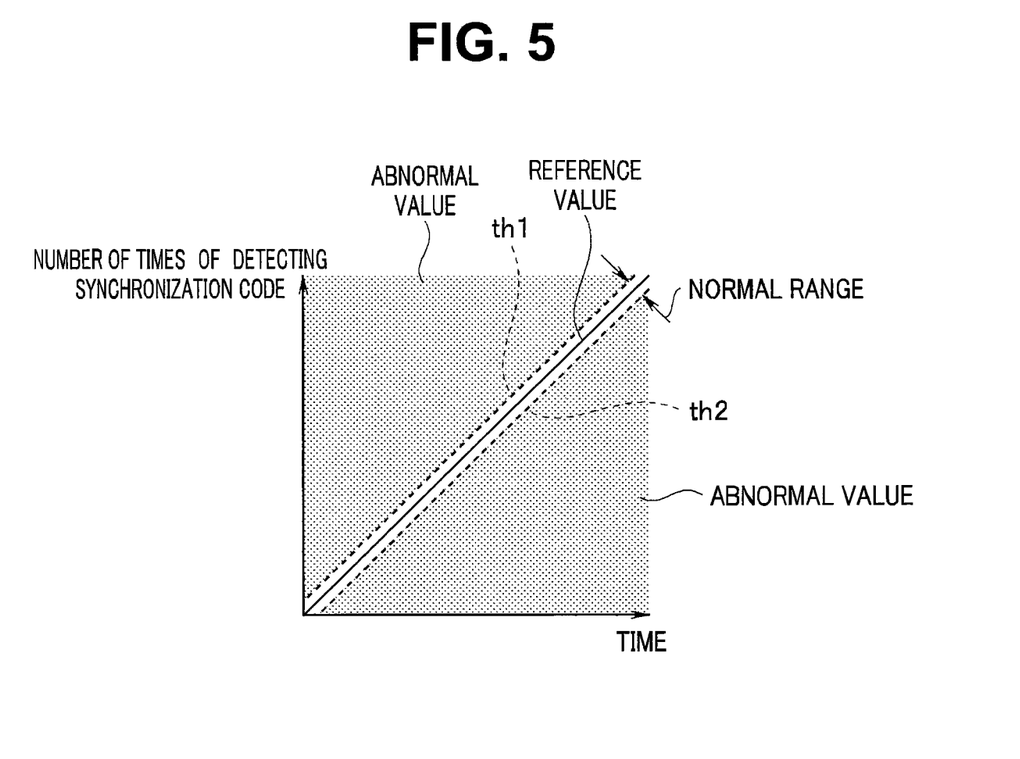
FIG. 5 is a diagram for describing one example of abnormality detection of a synchronization code.
Figure 6:
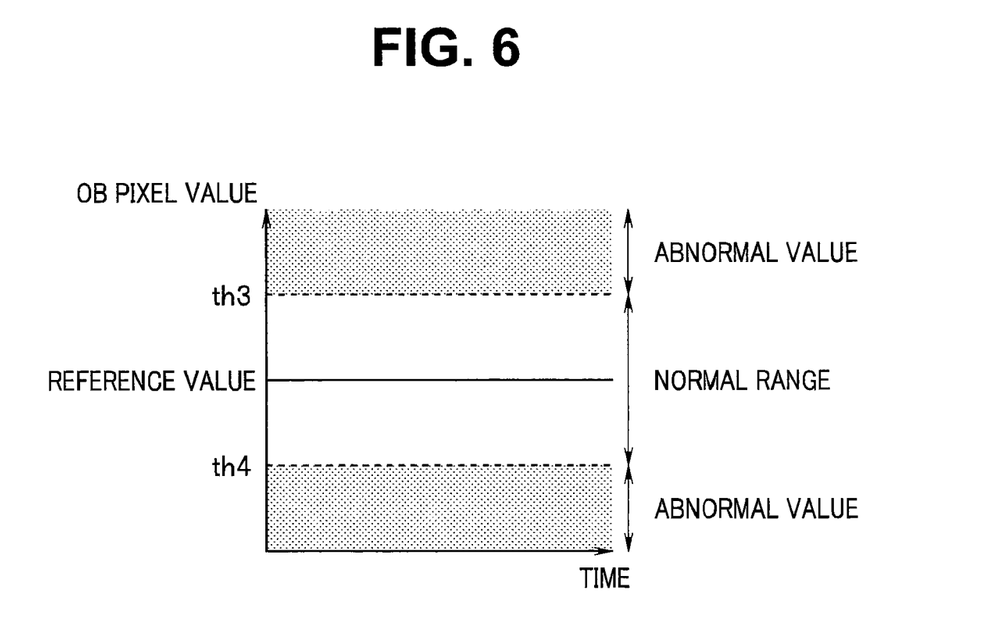
FIG. 6 is a diagram for describing one example of abnormality detection of an OB pixel value.
Figure 7:
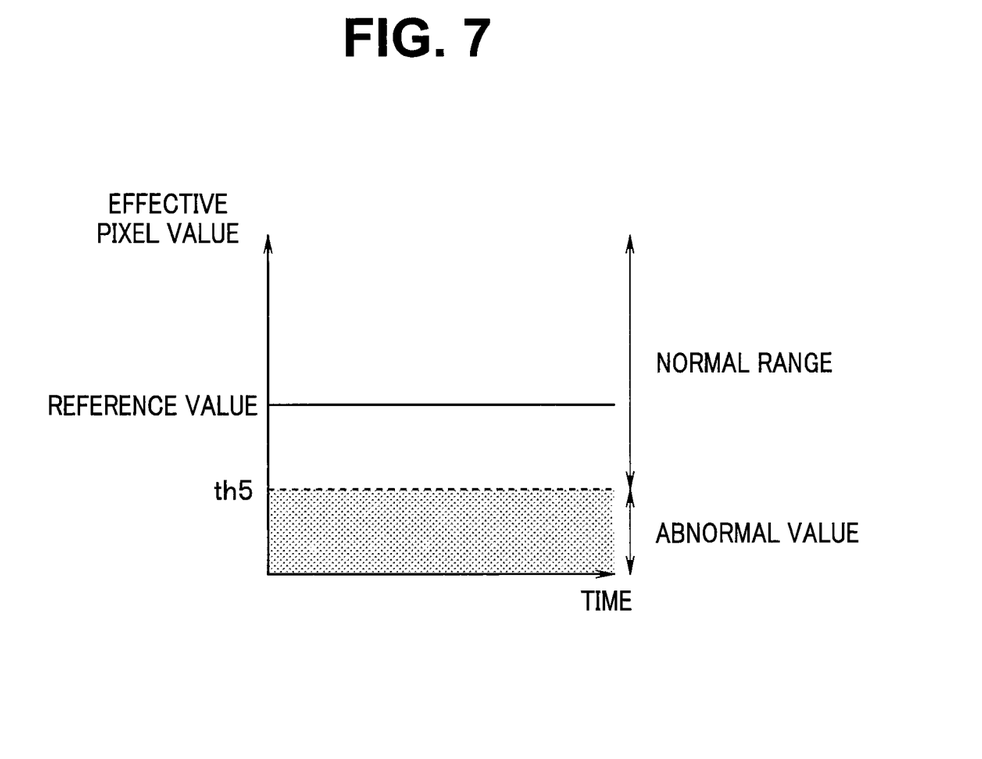
FIG. 7 is a diagram for describing one example of abnormality detection of an effective pixel value.
Figure 8:
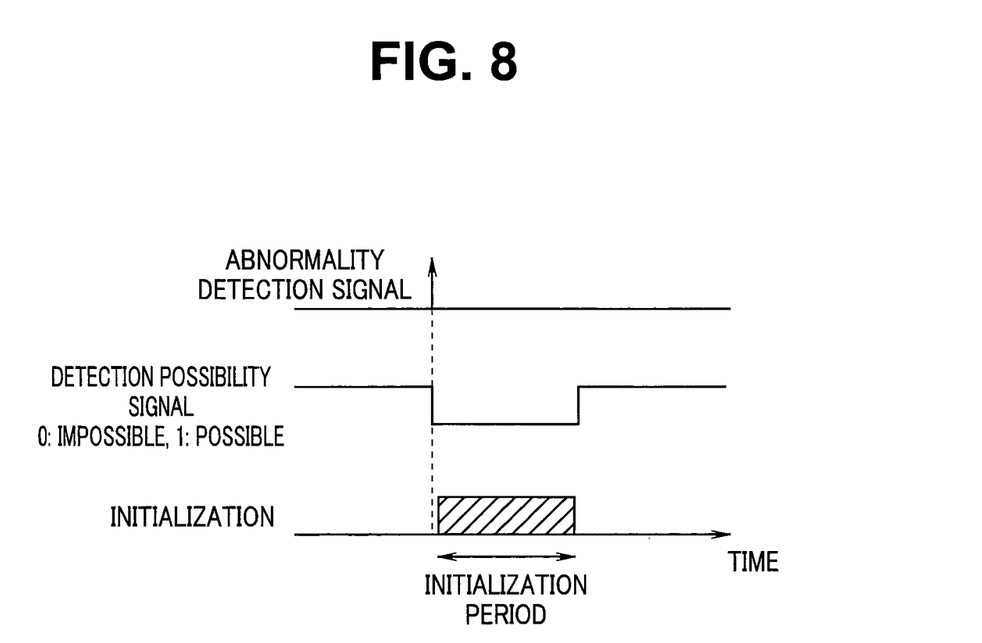
FIG. 8 is a diagram for describing one example of control of a drive control circuit when abnormality is present in an image pickup device 10.

FIG. 5 is a diagram for describing one example of the abnormality detection of the synchronization code, FIG. 6 is a diagram for describing one example of the abnormality detection of the OB pixel value, FIG. 7 is a diagram for describing one example of the abnormality detection of the effective pixel value, and FIG. 8 is a diagram for describing one example of control of the drive control circuit when the abnormality is present in the image pickup device 10.

The synchronization code monitoring portion 41 detects whether or not the number of times of detecting the synchronization code within a predetermined time period is the stipulated number of times. That is, the numbers of times that the number of times of receiving synchronizing signal is the number of times equal to or smaller than a threshold th1 and the number of times equal to or larger than a threshold th2 are counted. Specifically, it is considered that the synchronization code is detected when data that continues over four pixels of xFFF, xFFF, x000, x800 (hexadecimal notation in the case that the image pickup signal is of 12 bits) is decoded from a data arrangement of the image pickup signal, and the number of times of detection within a period of one field is counted.

Then, in the case that the number of times of receiving the synchronization code that is an abnormal value is equal to or larger than the stipulated number of times, the synchronization code monitoring portion 41 determines the abnormality of the image pickup device 10, and outputs the abnormality signal to the abnormality determination portion 44. Note that the synchronization code monitoring portion 41 determines the abnormality of the image pickup device 10 in the case that the number of times of receiving the synchronization code that is the abnormal value is equal to or larger than, or is equal to or smaller than the stipulated number of times, however, may determine the abnormality of the image pickup device 10 and output the abnormality signal in the case that the number of times of receiving the synchronization code that is the abnormal value becomes the stipulated number of times before the predetermined time elapses, for example. For example, while it is assumed that an abnormal state has occurred in the image pickup device 10 and the abnormality is determined in the case that the counted number of times is larger than 560 times or smaller than 540 times in contrast with 550 times that is the stipulated number of times at an end of the field, in the case of exceeding 560 times before the end of the field, the abnormality is determined at the point of time. A count number is cleared in the next field and counting is started again from an initial value.

The OB pixel monitoring portion 42 counts the number of pixels that are in a range of the abnormal value for the predetermined time period. That is, the OB pixel monitoring portion 42 counts the number of pixels, the OB pixel value of which is equal to or smaller than a threshold th3, and the number of pixels, the OB pixel value of which is equal to or larger than a threshold th4. Specifically, the number of times of receiving a value below the threshold of x0F0 for data corresponding to the value of one pixel of the image pickup signal and the number of times of receiving the value exceeding x110 for the data corresponding to the value of one pixel of the image pickup signal are counted.

Then, in the case that the number of pixels that are in the range of the abnormal value is equal to or larger than the stipulated number of pieces, the OB pixel monitoring portion 42 determines the abnormality of the image pickup device 10 and outputs the abnormality signal to the abnormality determination portion 44. Note that the count number is cleared in the next field and counting is started again from the initial value.

The effective pixel monitoring portion 43 counts the number of pixels that are in the range of the abnormal value for the predetermined time period. The threshold on a high luminance side does not exist in the effective pixel region, and the effective pixel monitoring portion 43 counts the number of pixels equal to or below a threshold th5 on a lower side of a dark reference value. Specifically, the number of times of receiving the value below the threshold of x0F0 for the data corresponding to the value of one pixel of the image pickup signal is counted.

Then, in the case that the number of pixels that are in the range of the abnormal value is equal to or larger than the stipulated number of pieces, the effective pixel monitoring portion 43 determines the abnormality of the image pickup device 10 and outputs the abnormality signal to the abnormality determination portion 44. Note that the count number is cleared in the next field and counting is performed from the initial value.

When one of the synchronization code monitoring portion 41, the OB pixel monitoring portion 42 and the effective pixel monitoring portion 43 outputs the abnormality detection signal, the abnormality determination portion 44 outputs the initialization start signal to the drive control circuit 19.

When the initialization start signal is inputted, the drive control circuit 19 initializes the image pickup device 10 again. Then, as illustrated in FIG. 8, the drive control circuit 19 turns the detection possibility signal from being possible (H level) to being impossible (L level) and outputs the signal to the monitoring portion 17 during an initialization period of the image pickup device 10. The drive control circuit 19 includes a timer not shown for example, and counts detection impossible time by the timer. In the case that the detection possibility signal indicate impossibility, the monitoring portion 17 does not determine the abnormality of the image pickup device 10.

In this way, the endoscope system 1 detects the abnormality for the synchronization code, the OB pixel value and the effective pixel value of the image pickup signal respectively, and initializes the image pickup device 10 again in the case that the abnormality is present in one of the synchronization code, the OB pixel value and the effective pixel value. For example, just by resetting control data of the register 15 of the image pickup device 10, in the case that the abnormality occurs in the image pickup signal due to the abnormality of the control data of the register 15, the abnormality of the image pickup signal cannot be immediately corrected. In contrast, the endoscope system 1 initializes the image pickup device 10 again when the abnormality of the synchronization code, the OB pixel value and the effective pixel value of the image pickup signal is detected so that the abnormality of the image pickup signal can be immediately corrected.

In addition, since the endoscope system 1 detects the abnormality for the synchronization code, the OB pixel value and the effective pixel value of the image pickup signal respectively, the abnormality of the image pickup signal can be surely detected.

Thus, according to the endoscope system of the present embodiment, operation abnormality of the solid-state image pickup device can be surely detected, and the operation abnormality of the solid-state image pickup device can be quickly returned to a normal state.

Note that, in the first embodiment, the control circuit 11 is provided in the connector portion 4c of the camera head, however, without being limited to the connector portion 4c, the control circuit 11 may be provided in the head portion 4a or the CCU 5 for example.

Second Embodiment

Next, the second embodiment will be described. In the second embodiment, the endoscope system in which the control circuit is provided in the head portion 4a of the camera head 4 will be described.

Figure 9:
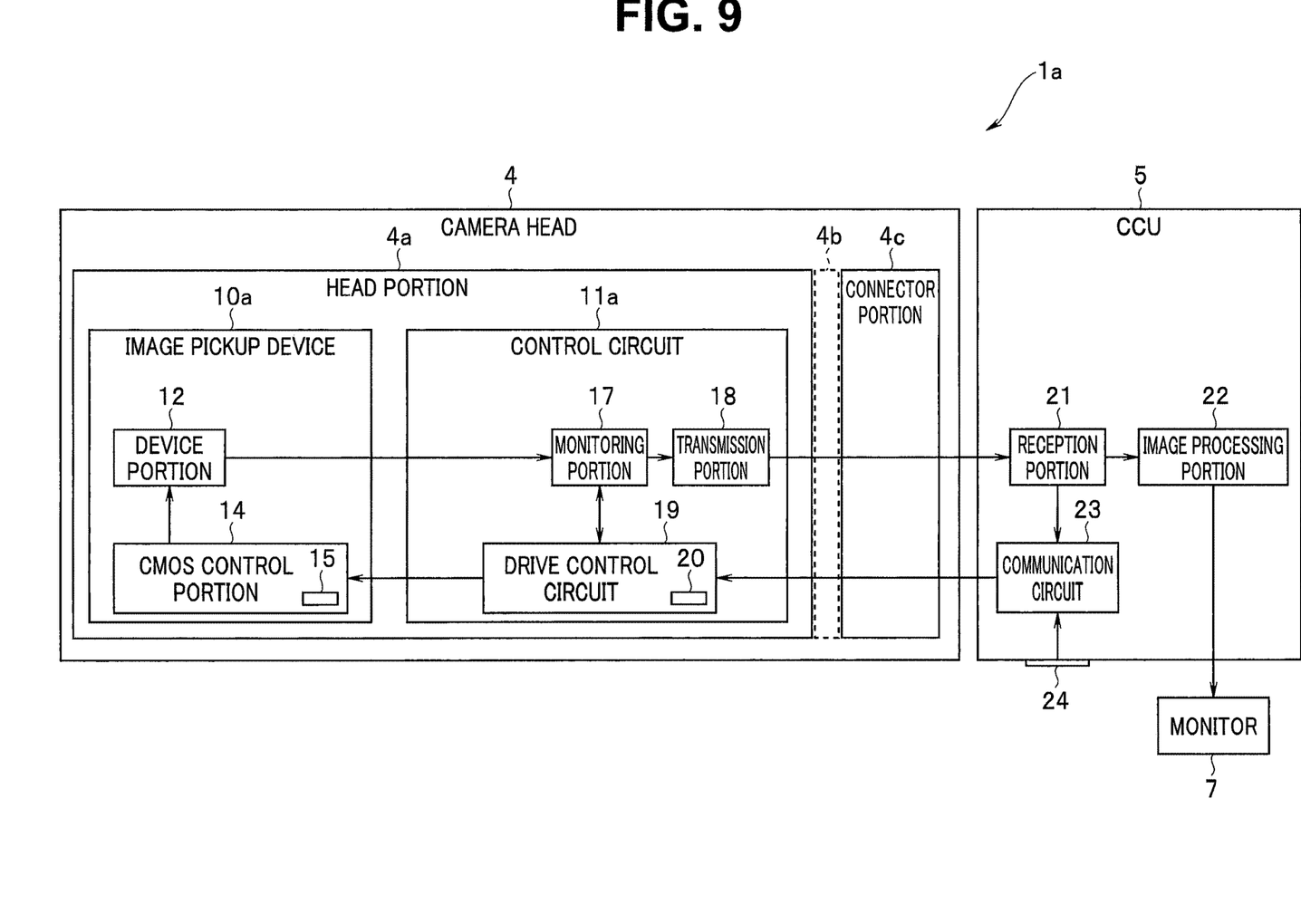
FIG. 9 is a diagram illustrating a detailed circuit configuration of a camera head and a camera control unit of an endoscope system relating to a second embodiment.

FIG. 9 is a diagram illustrating a detailed circuit configuration of the camera head and the camera control unit of the endoscope system relating to the second embodiment. Note that, in FIG. 9, for components similar to those in FIG. 2, same signs are attached and the description is omitted.

As illustrated in FIG. 9, an endoscope system 1a is configured including an image pickup device 10a and a control circuit 11a in the head portion 4a of the camera head 4. The image pickup device 10a is configured by eliminating the transmission portion 13 from the image pickup device 10 in FIG. 2. In addition, the control circuit 11a is configured by eliminating the reception portion 16 from the control circuit 11 in FIG. 2.

On the image pickup signal from the device portion 12, the synchronization code is superimposed by the control of the CMOS control portion 14, and the signal is inputted to the monitoring portion 17. The configuration of the monitoring portion 17 is similar to the configuration in FIG. 4 of the first embodiment. That is, the monitoring portion 17 outputs the inputted image pickup signal to the transmission portion 18, determines whether or not the abnormality is present in the image pickup signal, and in the case that the abnormality is present, outputs the initialization start signal to the drive control circuit 19. When the initialization start signal is inputted from the monitoring portion 17, the drive control circuit 19 initializes the image pickup device 10. The other configuration is similar to that of the first embodiment.

By such a configuration, the endoscope system of the present embodiment can surely detect the operation abnormality of the solid-state image pickup device and quickly return the operation abnormality of the solid-state image pickup device to the normal state, similarly to the first embodiment.

Third Embodiment

Next, the third embodiment will be described. In the third embodiment, the endoscope system in which the control circuit is provided in the CCU 5 will be described.

Figure 10:
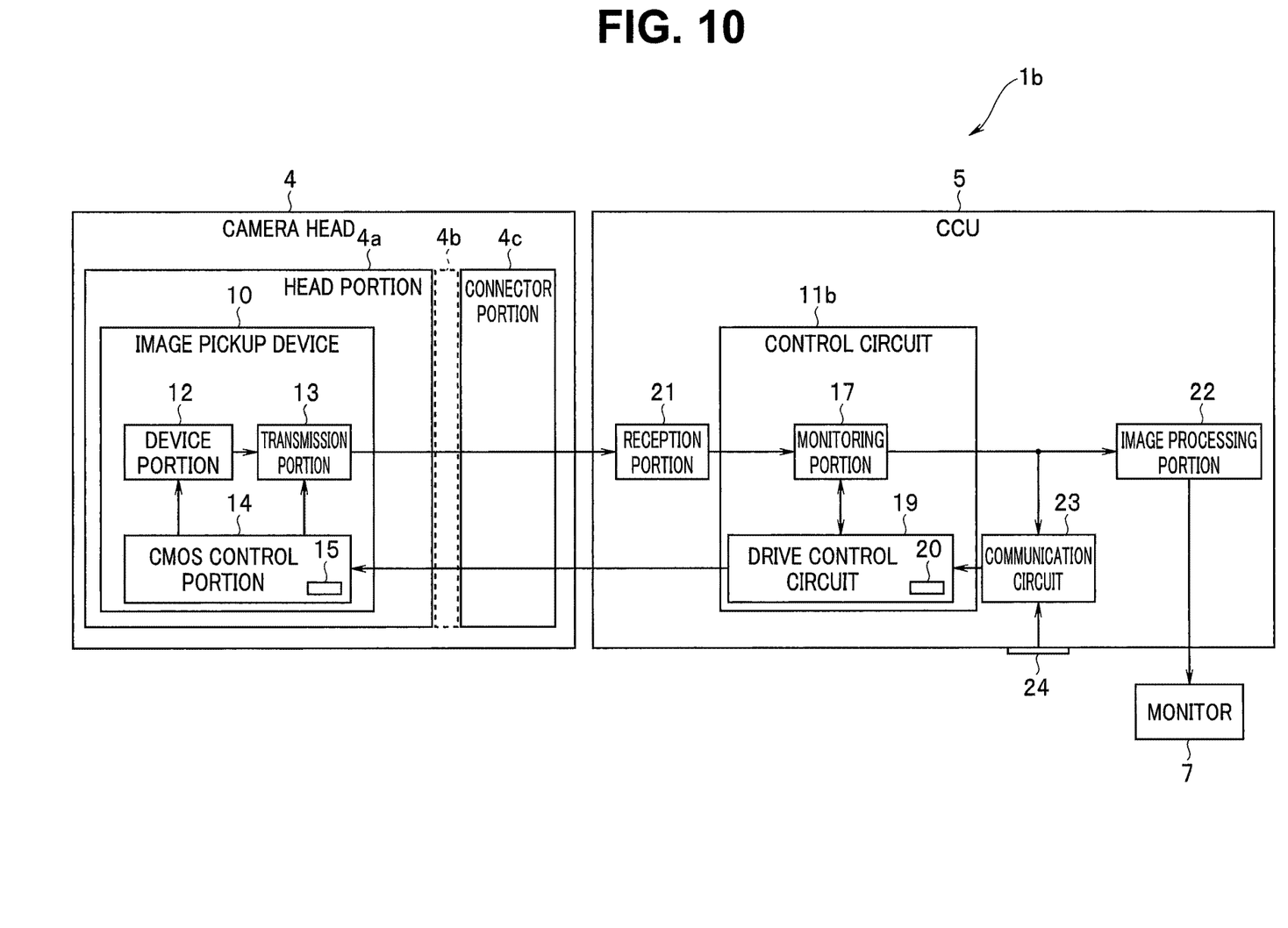
FIG. 10 is a diagram illustrating a detailed circuit configuration of a camera head and a camera control unit of an endoscope system relating to a third embodiment.

FIG. 10 is a diagram illustrating a detailed circuit configuration of the camera head and the camera control unit of the endoscope system relating to the third embodiment. Note that, in FIG. 10, for components similar to those of FIG. 2, same signs are attached and the description is omitted.

As illustrated in FIG. 10, an endoscope system 1b is configured including a control circuit 11b in the CCU 5. The control circuit 11b is configured by eliminating the reception portion 16 and the transmission portion 18 from the control circuit 11 in FIG. 2.

The transmission portion 13 converts the image pickup signal on which the synchronization code is superimposed from parallel to serial, and transmits the signal to the reception portion 21 of the CCU 5 as the LVDS. The reception portion 21 converts the received image pickup signal from serial to parallel, and outputs the signal to the monitoring portion 17.

The configuration of the monitoring portion 17 is similar to that of the configuration in FIG. 4 of the first embodiment. That is, the monitoring portion 17 outputs the inputted image pickup signal to the image processing portion 22, determines whether or not the abnormality is present in the image pickup signal, and in the case that the abnormality is present, outputs the initialization start signal to the drive control circuit 19. When the initialization start signal is inputted from the monitoring portion 17, the drive control circuit 19 initializes the image pickup device 10. The other configuration is similar to that of the first embodiment.

By such a configuration, the endoscope system of the present embodiment can surely detect the operation abnormality of the solid-state image pickup device and quickly return the operation abnormality of the solid-state image pickup device to the normal state, similarly to the first embodiment.

The present invention is not limited to the embodiments described above, and is also applicable to an electronic endoscope. Further, various changes and modifications or the like are possible without changing the gist of the present invention.

What is claimed is:

1. An endoscope system comprising:
   an image pickup device configured to pick up an image of an object;
   a drive control circuit configured to initialize and drive the image pickup device; and
   a monitoring circuit configured to detect abnormality of an image pickup signal from the image pickup device and output an initialization start signal to the drive control circuit,
   wherein the monitoring circuit compares a synchronization code, an optical black pixel value and an effective pixel value of the image pickup signal from the image pickup device with respective thresholds indicating a normal range and a stipulated number of times or a stipulated number of pixels, and in a case of detecting abnormality of one of the synchronization code, the optical black pixel value and the effective pixel value, outputs the initialization start signal to the drive control circuit, and
   the drive control circuit initializes the image pickup device in a case that the initialization start signal is inputted from the monitoring circuit.

2. The endoscope system according to claim 1, wherein, in a case that a number of times of detecting the synchronization code within a constant time period is off a predetermined threshold indicating the normal range and a number of times of detecting the synchronization code off the predetermined threshold exceeds a range of the stipulated number of times, the monitoring circuit outputs the initialization start signal to the drive control circuit.

3. The endoscope system according to claim 1,
   wherein the endoscope system comprises a camera head including a head portion and a connector portion integrally connected with the head portion through a cable, and
   the monitoring portion and the drive control circuit are provided in the connector portion.

4. The endoscope system according to claim 1,
   wherein the endoscope system comprises a camera head including a head portion and a connector portion integrally connected with the head portion through a cable, and
   the monitoring circuit and the drive control circuit are provided in the head portion.

5. The endoscope system according to claim 1, further comprising:
   a signal processor including a communication circuit capable of communicating with the drive control circuit; and
   a nonvolatile memory configured to store the respective thresholds and the stipulated number of pixels,
   wherein the respective thresholds and the stipulated number of times or the stipulated number of pixels stored in the nonvolatile memory can be changed through the communication circuit.

6. The endoscope system according to claim 5, wherein the monitoring circuit and the drive control circuit are provided in the signal processor.

7. The endoscope system according to claim 1, wherein, in a case that the optical black pixel value is off a predetermined threshold indicating the normal range and the number of optical black pixels off the predetermined threshold exceeds the stipulated number of pixels, the monitoring circuit outputs the initialization start signal to the drive control circuit.

8. The endoscope system according to claim 1, wherein, in a case that the effective pixel value is off a predetermined threshold indicating the normal range and the number of effective pixels off the predetermined threshold exceeds the stipulated number of pixels, the monitoring circuit outputs the initialization start signal to the drive control circuit.

* * * * *